United States Patent [19]
Gentry et al.

[11] Patent Number: 5,399,244
[45] Date of Patent: Mar. 21, 1995

[54] PROCESS TO RECOVER BENZENE FROM MIXED HYDROCARBONS BY EXTRACTIVE DISTILLATION

[75] Inventors: Joseph C. Gentry, Dallas, Tex.; Lloyd Berg, Bozeman, Mont.; John C. McIntyre, Hackettstown, N.J.; Randa W. Wytcherley, Belgrade, Mont.

[73] Assignee: Glitsch, Inc., Dallas, Tex.

[21] Appl. No.: 163,025

[22] Filed: Dec. 6, 1993

[51] Int. Cl.⁶ .......................... B01D 3/40; C07C 7/08
[52] U.S. Cl. ........................ 203/23; 203/51;
203/53; 203/56; 203/57; 203/58; 203/60;
203/63; 203/64; 203/69; 203/78; 203/79;
203/84; 585/807; 585/808; 585/857; 585/860;
585/862; 585/864; 585/865; 585/866; 585/867
[58] Field of Search ............ 203/57, 53, 23, 22,
203/51, 60, 63, 64, 69, 58, 56, 84, 85, 78, 79, 39;
585/804, 805, 807, 808, 860, 862, 856, 857, 865,
864, 866, 867

[56] References Cited

U.S. PATENT DOCUMENTS

| | | | |
|---|---|---|---|
| 4,793,90 | 12/1988 | Berg et al. | 203/51 |
| 2,655,467 | 10/1953 | Cooper et al. | 202/39.5 |
| 2,768,131 | 10/1956 | Lebeis et al. | 203/62 |
| 2,834,822 | 5/1958 | Worthington et al. | 203/65 |
| 2,842,484 | 7/1958 | Fleck | 202/39.5 |
| 3,005,032 | 10/1961 | Makin | 260/674 |
| 3,050,573 | 8/1962 | Anderson et al. | 260/681.5 |
| 3,114,783 | 12/1963 | Butler et al. | 260/674 |
| 3,227,632 | 1/1966 | Schmalenbach et al. | 208/313 |
| 3,338,824 | 8/1967 | Oliver | 208/313 |
| 3,681,202 | 8/1972 | Funkhouser | 203/53 |
| 3,689,372 | 9/1972 | Sugano et al. | 203/53 |
| 3,723,256 | 3/1973 | Thompson | 203/43 |
| 3,862,254 | 1/1975 | Eisenlohr et al. | 260/674 |
| 3,868,310 | 2/9175 | Yankleef et al. | 203/58 |
| 3,882,013 | 5/1975 | Katsobashvili | 208/60 |
| 3,884,769 | 5/1975 | Mikitenko et al. | 203/53 |
| 3,966,726 | 6/1976 | Toth et al. | 260/249.8 |

(List continued on next page.)

FOREIGN PATENT DOCUMENTS

| | | | |
|---|---|---|---|
| 499256 | 7/1976 | U.S.S.R. | 203/58 |
| 891606 | 1/1981 | U.S.S.R. | 585/866 |

OTHER PUBLICATIONS

G. H. Deal, Jr., H. D. Evans, E. D. Oliver, M. N. Papadopoulos, "A Better Way to Extract Aromatics," *Petroleum Refiner*, vol. 38, No. 9, 185–192, Sep. 1959.

J. Lautier, J. Durandet, C. Raimbault, M. Viguier, "Extraction of Aromatics With Dimethyl Sulfoxide," translated from *Revue de l'Institut Francais du Petrole*, 20, No. 1:181–190 (1965).

Axel Krause, "Dimethyl Sulfoxide Gets Tryout in New Aromatics–Extraction Process," *Chemical Engineering*, 54–56, Jan. 1966.

B. Choffe, C. Raimbault, F. P. Navarre, and M. Lucas, "Extract Aromatics With DMSO," *Hydrocarbon Processing*, vol. 45, No. 4 188–192, May 1966.

P. Bonnifay, B. Cha, J. Barbier, A. Vidal, B. Jugin, and R. Huin, "Maximizing Aromatics," *The Oil and Gas Journal*, 48, Jan. 19, 1976.

M. Devandran and B. K. Bhaskara Rao, "When Using Dimethyl Sulfoxide," *Hydrocarbon Processing*, 237, Nov. 1976.

(List continued on next page.)

*Primary Examiner*—Wilbur Bascomb, Jr.
*Attorney, Agent, or Firm*—Johnson & Wortley

[57] ABSTRACT

Benzene and other aromatics are separated from a stream of mixed hydrocarbons containing both aromatics and non-aromatics by extractive distillation with a solvent system containing dimethyl sulfoxide and optionally a co-solvent, preferably water, followed by distillation stripping of the aromatics from the enriched solvent system, and recycle of the lean solvent system to the extractive distillation step.

12 Claims, 1 Drawing Sheet

U.S. PATENT DOCUMENTS

| | | |
|---|---|---|
| 3,996,305 | 12/1976 | Berger .................................. 260/672 |
| 4,041,091 | 8/1977 | Henry ................................... 260/672 |
| 4,053,369 | 10/1977 | Cines ...................................... 203/52 |
| 4,152,217 | 5/1979 | Eisenberg et al. ..................... 203/23 |
| 4,162,198 | 7/1979 | Stockburger et al. ................ 203/23 |
| 4,363,704 | 12/1982 | Berg ....................................... 203/68 |
| 4,401,517 | 8/1983 | Lee ......................................... 203/53 |
| 4,488,937 | 12/1984 | Berg et al. ............................ 203/51 |
| 4,514,262 | 4/1985 | Berg ....................................... 203/51 |
| 4,585,526 | 4/1986 | Berg et al. ............................ 203/64 |
| 4,738,755 | 4/1988 | Berg et al. ............................ 203/51 |
| 4,801,357 | 1/1989 | Berg et al. ............................ 203/51 |
| 4,806,209 | 2/1989 | Berg et al. ............................ 203/51 |
| 4,822,947 | 4/1989 | Berg et al. ........................... 585/805 |
| 4,955,468 | 9/1990 | Lee ......................................... 203/53 |
| 5,032,232 | 7/1991 | Lee et al. ............................... 203/51 |
| 5,069,757 | 12/1991 | Brown .................................... 203/51 |
| 5,135,617 | 8/1992 | Brown et al. ......................... 203/56 |
| 5,145,562 | 9/1992 | Brown et al. ......................... 203/51 |

OTHER PUBLICATIONS

Fu–Ming Lee, "Use of Organic Sulfones as the Extractive Distillation Solvent for Aromatics Recovery," *Ind. Eng. Chem. Process Des. Dev.*, vol. 25, No. 4, 949–957 (1986).

Extracts from SRI International Report #182, 9, 49"56, 74–77, Jun. 1987.

Fu–Ming Lee and D. M. Coombs, "Two–Liquid–Phase Extractive Distillation for Aromatics Recovery," *Ind. Eng. Chem. Res.*, vol. 26, No. 3, 564–573 (1987).

Gaylord Chemical Corporation, Dimethyl Sulfoxide (DMSO) Reaction Solvent Technical Bulletin #105, Feb. 1992.

G. Emmerich, "Octenar, an Economical Process for Producing Low Benzene Gasoline," Report #AM-9-2-40 presented at the 1992 NPRA Annual Meeting, Mar. 22, 1992.

R. E. Brown and Fu–Ming Lee, "Effect of Packing on Distillation Columns With High Liquid to Vapor Ratios," presentation at the AIChE Annual Meeting, Nov. 1, 1992.

B. A. Todd and Fu–Ming Lee, "Two Liquid Phases in Extractive Distillation for Aromatic Recovery," presenation at the AIChE Summer National Meeting, Aug. 17, 1993.

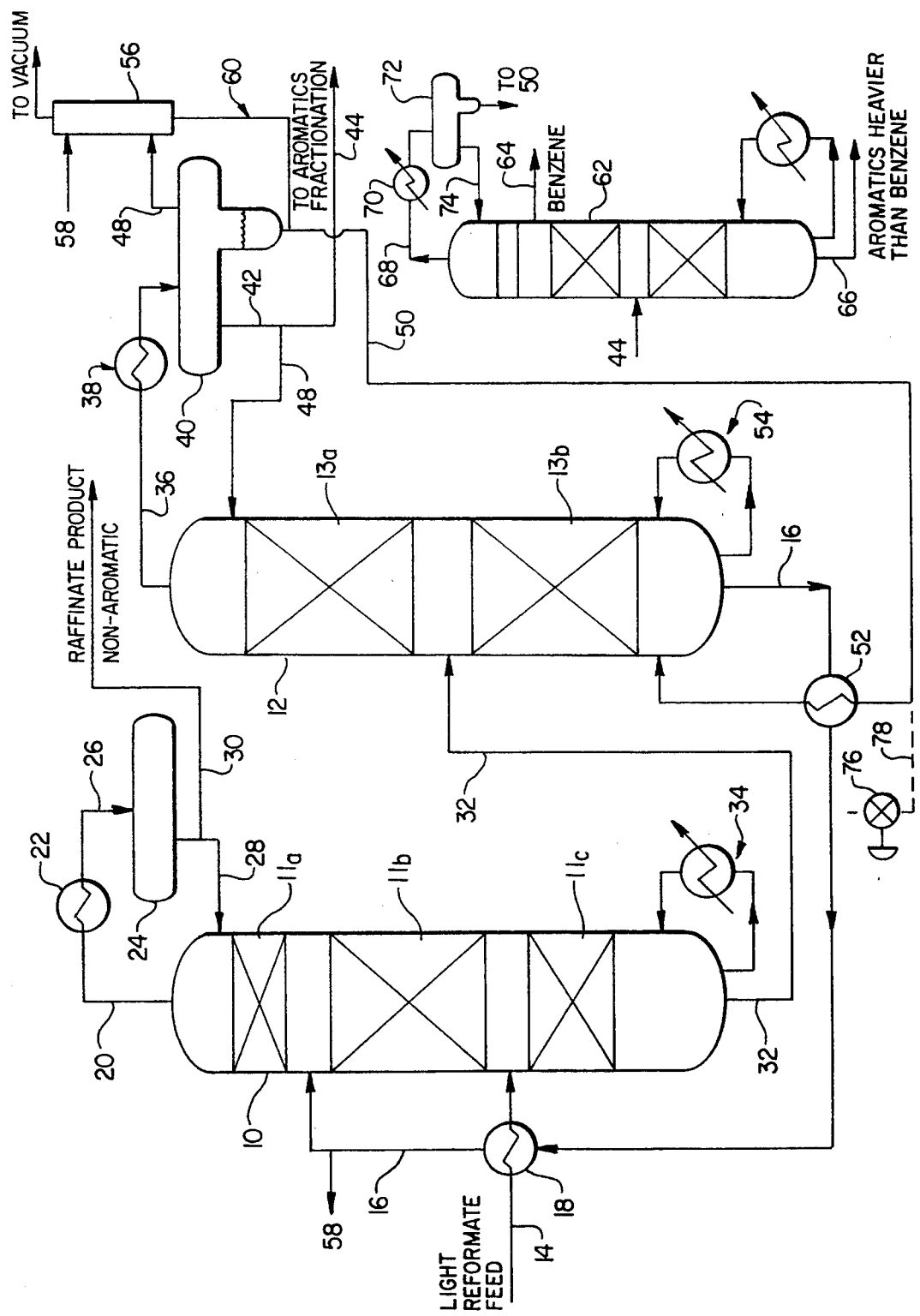

PROCESS TO RECOVER BENZENE FROM MIXED HYDROCARBONS BY EXTRACTIVE DISTILLATION

BACKGROUND OF THE INVENTION

This invention relates to a method or process for removing and recovering benzene and/or other aromatic hydrocarbons from a mixed stream of hydrocarbons, typically a stream of the kind intended to be worked up into a finished gasoline. Feed sources such as pyrolysis gasoline, catalytic reformate, or coal tar liquids may be sources of the mixed hydrocarbon stream utilized in the process. Many similar relatively light hydrocarbon streams containing benzene as well as other aromatic hydrocarbons are utilized to formulate finished gasoline. At one time, benzene and other aromatics were not considered objectionable components of gasoline, and were even regarded favorably because of their high octane numbers, but the situation is now changing because of governmental restrictions being placed on the amount of benzene considered acceptable in finished gasolines. Furthermore, benzene, and other aromatic hydrocarbons, are more valuable in their own right as starting materials for important petrochemical products, and have greater value in such uses than as fuel. For reasons such as these, there is an increasing need for efficient and economical processes for separating benzene from mixed hydrocarbon streams, and it is an object of the present invention to provide such a process.

SUMMARY OF THE INVENTION

In accordance with the present invention, a method or process is provided for recovering benzene and other aromatic hydrocarbons from a mixed stream containing them as well as non-aromatic hydrocarbons. The process involves extractive distillation of the benzene-containing mixed hydrocarbon feed stock in the presence of an extractive distillation solvent system which is dimethyl sulfoxide (DMSO) and optionally one or more co-solvents, preferably water. In the extractive distillation step, the non-aromatic hydrocarbons form the overhead raffinate stream. A bottoms stream containing the solvent system enriched by the dissolved benzene and/or other aromatic hydrocarbons is passed from the distillation column as a bottoms stream separate from the overhead stream, thus effecting the separation of the aromatics from the other hydrocarbons. The bottoms stream is then subjected to a stripping operation in which the aromatics are removed as an overhead product, together with a minor amount of dimethyl sulfoxide and water (if used), and the bottoms product from the stripping step is a solvent system which is lean in benzene or other aromatics.

The overhead stream from the stripping step may be condensed, and phase-separated to separate the dimethyl sulfoxide and water solvent system from the aromatics, so that they may be passed on to further processing, while the solvents are recycled to the stripper.

DMSO is highly selective of benzene and other aromatics and highly rejective of the non-aromatics, so much so that the formation of two liquid phases may be noted in the extractive distillation step under some conditions. The presence of such two phases does not impair the efficacy of the process, however.

The use of a co-solvent with the DMSO is optional, and if one is used, it is preferably water. As will be discussed below, water may be used to adjust the solvency and selectivity of the DMSO. It also facilitates the stripping operation, and permits lower bottoms temperatures in both columns.

In a primary aspect, a method according to the invention successfully removes and recovers benzene and/or other aromatic hydrocarbons from a mixed stream containing benzene and/or other aromatic hydrocarbons together with mixed non-aromatic hydrocarbons. The mixed hydrocarbon stream is extractively distilled with DMSO, and optionally a co-solvent, preferably water, in a vapor-liquid contacting column. In this manner, there is derived from said mixed hydrocarbon stream and extractive distillation solvent system an overhead raffinate stream made up primarily of the mixed non-aromatic hydrocarbons and a bottoms stream made up primarily of benzene and/or other aromatic hydrocarbons, dissolved in dimethyl sulfoxide and water (preferably) of the extractive distillation solvent system.

The overhead raffinate stream is a product stream which has been improved by the removal of the benzene from it. The bottoms stream is an intermediate product stream containing both the separated benzene and/or other aromatic hydrocarbons, and the constituents of the extractive distillation solvent system, usually dimethyl sulfoxide (and water). This mixed bottoms stream is further treated in a stripping column, where it is distilled to obtain a stripper overhead stream containing the benzene and/or other aromatic hydrocarbons and part of the dimethyl sulfoxide (and water). The bottoms stream from the stripper contains primarily dimethyl sulfoxide (and water). These materials are preferably recycled to the extractive distillation column for reuse and extractive distillation with the incoming mixed hydrocarbon stream feed stock.

The overhead stream from the stripper is preferably condensed and allowed to gravity separate into fractions, the light fraction being the aromatic product stream containing benzene and/or aromatic hydrocarbons, and the heavy fraction containing dimethyl sulfoxide (and water).

The dimethyl sulfoxide (and water) may be recycled to the stripping column.

In the course of being recycled, the solvent stream drawn from the overhead of the stripping column may be heat exchanged with the bottoms stream from the stripper, or otherwise, and returned as stripping vapor to the stripping column.

BRIEF DESCRIPTION OF THE DRAWING

The drawing is an elevational simplified process diagram illustrating the method or process of the invention and showing very diagrammatically the equipment involved.

DESCRIPTION OF THE PREFERRED EMBODIMENTS

In the drawing, it can be seen that the method of the invention can be practiced by the use of two primary columns, column 10 being an extractive distillation column and column 12 being a stripper column. A mixed stream containing benzene and/or other aromatic hydrocarbons, together with non-aromatic hydrocarbons is fed into extractive distillation column 10 through line 14 at a lower mid-region of the column. In the drawing, the feed stock passing through line 14 is labelled "light reformate feed," since this is a typical feed stock containing both aromatics and non-aromatics. Line 16 feeds into the upper middle region of extractive distillation column 10, a two-phase extractive distillation solvent system containing primarily dimethyl sulfoxide (and water). This solvent system flows downwardly through the column in countercurrent flow with respect to the lighter components of the feed entering through line 14. The extractive distillation solvent system flowing through line 16 may be heat exchanged with the light reformate feed flowing through line 14 in heat exchanger 18 to remove heat from the solvent system and add heat to the feed.

The extractive distillation in column 10 produces an overhead stream leaving the column through line 20 at the top; this overhead stream is cooled in a condenser 22 and passes into drum 24 through line 26. A reflux stream is returned to a point near the top of column 10 through line 28 while the liquid product stream, consisting primarily of a non-aromatic mixed hydrocarbon raffinate stream leaves the unit through line 30.

At the bottom of column 10, rich solvent leaves through line 32. A portion of the liquid at the bottom of the tower is passed through a reboiler circuit 34 where it is heat exchanged with low pressure steam. It is a particular advantage of the present invention that the operating conditions are such that low pressure steam is a suitable and convenient heat source for operating the extractive distillation column reboiler. This makes expensive high pressure steam or other expensive heat sources unnecessary.

Column 10 is illustrated as a tower with three sections of structured or random packing mounted therein at 11a, 11b, 11c, but other liquid-vapor contact devices, such as trays, may be employed if desired.

As was mentioned above, rich solvent containing the benzene and/or aromatic hydrocarbons is passed to stripper 12 through line 32. Conditions are maintained within the stripper which result in an overhead stream leaving the top of stripper column 12 through line 36. This stream is condensed in heat exchanger 38 and flows into separator drum 40, where the light aromatics phase-separate from the heavier solvent by difference of density. Line 42 carries the separated aromatics, which are the lighter stream in drum 40, to further processing by way of line 44 or to reflux through line 46. A vacuum is drawn on drum 40 through line 48. The heavier separated material from drum 40 passes through line 50 back to the lower region of stripper column 12. As it is so routed, it may be heat exchanged in heat exchanger 52 with the lean two-phase solvent leaving the bottom of stripper 12 through line 16. The stream passing through line 50 may be bypassed into line 16 through line 78, equipped with valve 76. Heat may conveniently be supplied to the stripper column 14 through reboiler circuit 54. Again, it is an advantage of the present invention that operating conditions are such that low pressure steam may be used to operate reboiler circuit 54.

Stripper column 12 is shown as being packed with two sections of structured packing or random packing 13a, 13b, although other liquid-vapor contact means, such as trays, may be employed if desired.

While dimethyl sulfoxide, one of the components of the two-phase extractive distillation solvent system, is known as an extractive distillation solvent in various other extractive distillation contexts, it has been found here that it is particularly effective in enhancing the relative volatility of the non-aromatic hydrocarbons with respect to the aromatic hydrocarbons. It therefore gives enhanced selectivity. The selectivity of DMSO for benzene and other aromatics and its concomitant rejectivity of non-aromatics is indicated by the beforementioned observation of two liquid phases in the extractive distillation step. Although the design and operation of a distillation column with two liquid phases has generally been avoided because of the difficulty in mixing the phases, we have found that the greater selectivity of the DMSO (and water) in a properly designed system more than offsets any loss of efficiency that may be encountered in the extractive distillation operation. A comparison of DMSO with other extractive distillation solvents for benzene is given in Table 1.

TABLE 1

SOLVENT COMPARISONS FOR BENZENE RECOVERY BY EXTRACTIVE DISTILLATION

| Solvent | ALPHA Cyclo $C_6$/BZ |
|---|---|
| #No agent | 1.0 |
| Sulfolane | 2.2* |
| NMP | 2.0 |
| Morpholine | 1.6 |
| DMSO | 2.4* |
| Adiponitrile | 2.1* |
| Dimethyl acetamide | 1.9 |

Test made in an Othmer-type VLE still at atmospheric pressure.
All relative volatilities were measured at a 1:1 solvent:Feed ratio.
*Apparent relative volatility; forms 2 liquid phases.
Benzene and cyclohexane forms a minimum-boiling azeotrope and cannot be separated by conventional distillation; hence, the relative volatility with no agent present is unity.

Co-solvents may be employed to alter the characteristics of the primary solvent in the three ways:

1) Improve the selectivity of the primary solvent;
2) Facilitate the stripping of the aromatics from the primary solvent; and
3) Reduce the operating temperature at the base of the two distillation columns for a given operating pressure. To achieve the objectives of #2 and #3, the nbp of the co-solvent should generally be lower than the nbp of DMSO (189° C.), but not so low as to cause difficulty in separating the extracted aromatics from the co-solvent. Suitable (non-limiting) examples of possible co-solvents are: dimethylformamide (DMF), methoxybenzene, ethylene glycol, mixed xylenes, morpholine, ethylene glycol butyl ether, di-methyl acetamide, n-ethyl morpholine, and water.

A combination of two or more co-solvents may be required or desired to achieve the optimum performance of the solvent system.

The use of water (as a co-solvent) is optional. It has been discovered that water, the preferred co-solvent, has three important functions or effects in accordance with the invention. First, it may be used in the solvent as an important controllable variable for providing ultimate control of the percent recovery of the aromatics and their as-recovered purity, because it affects the selectivity of the DMSO. In general, water increases the selectivity of the DMSO for dissolving the aromatics and increases the rejectivity of the DMSO for non-aromatics, while reducing the solvency of all hydrocarbons in the solvent.

Second, water increases the ease with which the aromatics may be stripped from the solvent in the stripper.

Third, it permits the use of lower bottoms temperatures in both the extractive distillation column and the stripper column.

It should also be noted that the water is operated in a closed loop, and that there is no waste water stream.

The dimethyl sulfoxide has other characteristics which make it a particularly desirable component of the extractive distillation solvent system. It is chemically and thermally stable at the operating conditions of the process. It is low cost, relatively non-toxic, easily biodegradable, and it is non-corrosive to carbon steel, which makes possible relatively inexpensive construction of the columns involved.

The presently preferred operating conditions for the process of the invention are summarized in Table 2:

TABLE 2

Preferred Operating Conditions

| | Range | More Preferred |
| --- | --- | --- |
| R/D Extractive Distillation | 0.2–5.0 | 0.8–2.0 |
| Operating Temperatures | dependent on boiling range of feed stock | |
| Operating Pressure, ED Column | 4–60 psia | 14.7–30 psia |
| Operating Pressure, Stripper | 1–20 psia | 1.5–5 psia |
| Solvent: Feed, weight ratio | 1:1–12:1 | 2:1–6:1 |
| Lean solvent water content, wt % | 0–10% | 0.2–4.0% |
| R/D Stripper | 0.2–4.0 | 0.5–1.5 |
| Vent scrubber, lean solvent:vapors, wt ratio | 0.5–40.0 | 2.0–5.0 |
| Stripper column, stripping ratio:aromatics, wt ratio | 0–0.50 | 0.01–0.10 |

It should be noted that vacuum line 48 includes a solvent scrubber 56 of known type to remove traces of aromatics that might otherwise escape into the environment.

For example, a portion of the lean solvent flowing through line 16 to column 10 may be drawn off through line 58 and delivered to scrubber 56 and flowed downwardly therethrough countercurrently to aromatic vapors introduced to the lower part of the scrubber through line 48 from drum 46. The aromatic vapors are dissolved into the solvent which leaves the scrubber through line 60. Line 60 delivers the enriched solvent into line 50 for recycle to stripper 12.

The stream of mixed aromatics which has been recovered by the process of the invention passing through line 44 may be fractionated in accordance with the invention by being delivered into fractionating column 62, where it is separated into benzene, removed through side stream line 64 and aromatics heavier than benzene removed through bottoms line 66. The overhead stream leaves column 62 through line 68 and is condensed at exchanger 70 and passed into drum 72. The hydrocarbon portion of the condensate is passed through line 74 to column 62 as reflux, and the water portion is drawn off through line 76 to recycle line 50.

OPERATING EXAMPLES

The operation of the invention may be further understood through a consideration of the following examples:

Example 1 — Extractive Distillation of a Catalytic Reformate Hydrocarbon Fraction A stream derived from a catalytic reformate was prefractionated to achieve the following composition:

| Component | Wt Fraction |
| --- | --- |
| Benzene | 19.9% |
| Toluene | 20.0% |
| $C_8$ Aromatics | 16.4% |
| $C_9+$ Aromatics | 1.0% |

-continued

| Component | Wt Fraction |
| --- | --- |
| $C_5$ Non-aromatics | 7.3% |
| $C_6$ Non-aromatics | 19.9% |
| $C_7$ Non-aromatics | 14.3% |
| $C_8+$ Non-aromatics | 1.2% |

This was preheated to 87° C. and fed into an extractive distillation column operating at atmospheric pressure. A solvent mixture consisting of DMSO with 2.1 wt % water was fed into an upper zone at 61° C. Reflux was returned to the column at a 1:1 ratio with the overhead product. This operation yielded an overhead raffinate stream containing 0.44 wt % benzene, 0.02 wt % toluene, and the balance non-aromatics. The bottoms product contained the major part of the solvent, water, and aromatics, and 0.3% n-heptane with much lower quantities of lower-boring non-aromatics. This indicates that a benzene fraction may be derived by subsequent conventional distillation which would be substantially free of non-aromatics.

Example 2 — Solvent Stripping

Extract material from an extractive distillation run was fed to an intermediate point in a solvent stripper column operated at 100 mmHg absolute pressure. The column was reboiled and live steam was supplied at the base of the column at a rate of 0.17:1.0 weight ratio to aromatic product. The overhead was divided into an upper phase of essentially aromatic and heavy non-aromatic hydrocarbons and a lower phase of essentially DMSO and water. A portion of the upper phase was returned to the column as reflux at a ratio of 1:1 with the product draw. The lower phase contained 15% DMSO with the balance being water. The bottoms product, being stripped of essentially all the hydrocarbons, was composed of DMSO with 0.6% water and <10 ppm of $C_6$–$C_8$ aromatics.

What is claimed is:

1. A method for removing and recovering benzene and/or other aromatic hydrocarbons from a mixed stream containing benzene and/or other aromatic hydrocarbons and mixed non-aromatic hydrocarbons comprising:

flowing said mixed stream in countercurrent contact with an extractive distillation solvent system consisting essentially of dimethyl sulfoxide in an extractive distillation column to thereby extractively distill said mixed stream and extractive distillation solvent system to obtain an overhead raffinate stream consisting essentially of said mixed non-aromatic hydrocarbons and a bottoms stream consisting essentially of said benzene and/or other aromatic hydrocarbons, dissolved and/or dispersed in said distillation solvent system;

distilling said bottoms stream in a stripping column to obtain a stripper overhead stream containing said benzene and/or other aromatic hydrocarbons and part of said distillation solvent system, and a stripper bottoms stream consisting essentially of components of said distillation solvent system;

recycling said stripper bottoms stream to said extractive distillation column for extractive distillation with said mixed stream;

separating the stripper overhead stream by condensation and phase separation into an aromatic product stream containing benzene and/or other aromatic hydrocarbons and a solvent stream containing components of said distillation solvent system.

2. A method in accordance with claim 1 and further comprising recycling said solvent stream to said stripping column.

3. A method in accordance with claim 2 and further comprising heat exchanging said solvent stream being recycled to said stripping column with said distillation column bottoms stream.

4. A method in accordance with claim 1 and further comprising fractionating said stripper overhead stream after separation of said solvent stream therefrom to obtain a benzene stream and a stream of aromatics heavier than benzene.

5. A method for removing and recovering benzene and/or other aromatic hydrocarbons from a mixed stream containing benzene and/or other aromatic hydrocarbons and mixed non-aromatic hydrocarbons comprising:

flowing said mixed stream in countercurrent contact with an extractive distillation solvent system consisting essentially of dimethyl sulfoxide and water in an extractive distillation column to thereby extractively distill said mixed stream and extractive distillation solvent system to obtain an overhead raffinate stream consisting essentially of said mixed non-aromatic hydrocarbons and a bottoms stream consisting essentially of said benzene and/or other aromatic hydrocarbons, dissolved and/or dispersed in said distillation solvent system;

distilling said bottoms stream in a stripping column to obtain a stripper overhead stream containing said benzene and/or other aromatic hydrocarbons and pan of said distillation solvent system, and a stripper bottoms stream consisting essentially of components of said distillation solvent system;

recycling said stripper bottoms stream to said extractive distillation column for extractive distillation with said mixed stream;

separating the stripper overhead stream by condensation and phase separation into an aromatic product stream containing benzene and/or other aromatic hydrocarbons and a solvent stream containing components of said distillation solvent system.

6. A method in accordance with claim 5 and further comprising recycling said solvent stream to said stripping column.

7. A method in accordance with claim 6 and further comprising heat exchanging said solvent stream being recycled to said stripping column with said distillation column bottoms stream.

8. A method in accordance with claim 5 and further comprising fractionating said stripper overhead stream after separation of said solvent stream therefrom to obtain a benzene stream and a stream of aromatics heavier than benzene.

9. A method for removing and recovering benzene and/or other aromatic hydrocarbons from a mixed stream containing benzene and/or other aromatic hydrocarbons and mixed non-aromatic hydrocarbons comprising:

flowing said mixed stream in countercurrent contact with an extractive distillation solvent system consisting essentially of dimethyl sulfoxide and at least one co-solvent selected from the class consisting of dimethyl formamide, methoxybenzene, ethylene glycol, mixed xylenes, morpholine, ethylene glycol butyl ether, all-methyl acetamide, n-ethyl morpholine, water, and mixtures thereof in an extractive distillation column to thereby extractively distill said mixed stream and extractive distillation solvent system to obtain an overhead raffinate stream consisting essentially of said mixed non-aromatic hydrocarbons and a bottoms stream consisting essentially of said benzene and/or other aromatic hydrocarbons, dissolved and/or dispersed in said distillation solvent system;

distilling said bottoms stream in a stripping column to obtain a stripper overhead stream containing said benzene and/or other aromatic hydrocarbons and part of said distillation solvent system, and a stripper bottoms stream consisting essentially of components of said distillation solvent system;

recycling said stripper bottoms stream to said extractive distillation column for extractive distillation with said mixed stream;

separating the stripper overhead stream by condensation and phase separation into an aromatic product stream containing benzene and/or other aromatic hydrocarbons and a solvent stream containing components of said distillation solvent system.

10. A method in accordance with claim 9 and further comprising recycling said solvent stream to said stripping column.

11. A method in accordance with claim 10 and further comprising heat exchanging said solvent stream being recycled to said stripping column with said distillation column bottoms stream.

12. A method in accordance with claim 9 and further comprising fractionating said stripper overhead stream after separation of said solvent stream therefrom to obtain a benzene stream and a stream of aromatics heavier than benzene.

* * * * *

UNITED STATES PATENT AND TRADEMARK OFFICE
CERTIFICATE OF CORRECTION

PATENT NO. : 5,399,244
DATED : March 21, 1995
INVENTOR(S) : Joseph C. Gentry, et al.

It is certified that error appears in the above-indentified patent and that said Letters Patent is hereby corrected as shown below:

| | | |
|---|---|---|
| Column 3, line 42 | Delete "fight" | Insert --light-- |
| Column 3, line 46 | Delete "fine" | Insert --line-- |
| Column 3, line 48 | Delete "fine" | Insert --line-- |
| Column 3, line 55 | Delete "14" | Insert --12-- |
| Column 5, line 37 | Delete "46" | Insert --40-- |
| Column 5, line 52 | Delete "through line 76" | |
| Column 6, line 19 | Delete "lower-boring" | Insert --lower-boiling-- |
| Column 7, line 34 | Delete "pan" | Insert --part-- |
| Column 8, line 17 | Delete "all-methyl" | Insert --di-methyl-- |

UNITED STATES PATENT AND TRADEMARK OFFICE
CERTIFICATE OF CORRECTION

PATENT NO. : 5,399,244

DATED : March 21, 1995

INVENTOR(S) : Joseph C. Gentry, et al.

It is certified that error appears in the above-indentified patent and that said Letters Patent is hereby corrected as shown below:

In the drawing, the reference numeral 48, adjacent to reference numeral 13a, should read 46.

Signed and Sealed this

Twenty-second Day of October, 1996

Attest:

BRUCE LEHMAN

*Attesting Officer*        Commissioner of Patents and Trademarks